(12) United States Patent
Wiens

(10) Patent No.: US 8,398,574 B1
(45) Date of Patent: Mar. 19, 2013

(54) ATHLETIC GARMENT WITH INFLATABLE CUP PROTECTOR ASSEMBLY

(76) Inventor: Joel J. Wiens, Eagan, MN (US)

( * ) Notice: Subject to any disclaimer, the term of this patent is extended or adjusted under 35 U.S.C. 154(b) by 644 days.

(21) Appl. No.: 12/592,939

(22) Filed: Dec. 4, 2009

Related U.S. Application Data

(60) Provisional application No. 61/201,814, filed on Dec. 15, 2008.

(51) Int. Cl.
*A61F 13/00* (2006.01)
*A41D 13/00* (2006.01)

(52) U.S. Cl. ............. 602/68; 602/13; 602/67; 128/98.1; 128/891; 128/DIG. 20; 2/466; 2/DIG. 3

(58) Field of Classification Search .................. 602/13, 602/67–73; 2/466, DIG. 3, 227, 228, 403; 128/98.1, 118.1, 891, DIG. 20
See application file for complete search history.

(56) References Cited

U.S. PATENT DOCUMENTS

| | | | | |
|---|---|---|---|---|
| 1,074,147 A | * | 9/1913 | Whitlock | 602/70 |
| 1,686,943 A | * | 10/1928 | Tritch | 602/70 |
| 1,691,658 A | * | 11/1928 | Kennedy | 602/70 |
| 1,830,572 A | * | 11/1931 | Taylor | 602/72 |
| 3,043,292 A | | 7/1962 | Mendelson | |
| D252,116 S | | 6/1979 | DiMatteo | |
| 4,453,541 A | * | 6/1984 | Castelli et al. | 602/72 |
| 5,134,726 A | | 8/1992 | Ross | |
| 5,383,893 A | * | 1/1995 | Daneshvar | 606/201 |
| 5,423,852 A | * | 6/1995 | Daneshvar | 606/201 |
| 5,628,721 A | * | 5/1997 | Arnold et al. | 602/19 |
| 5,984,910 A | | 11/1999 | Berke | |
| 6,048,327 A | * | 4/2000 | Kieffer | 602/70 |
| 6,338,164 B1 | * | 1/2002 | Howard | 2/242 |
| 6,635,038 B2 | | 10/2003 | Scovel | |
| 7,141,043 B2 | | 11/2006 | Harvie | |
| 7,178,176 B1 | * | 2/2007 | S-Cronenbold | 2/466 |
| D571,532 S | | 6/2008 | Gutierrez | |
| D579,628 S | | 11/2008 | Wiens | |
| D595,902 S | | 7/2009 | Wiens | |
| 7,578,009 B1 | | 8/2009 | Boston | |
| D608,951 S | | 1/2010 | Wiens | |
| 7,716,755 B1 | * | 5/2010 | Wiens | 2/466 |
| 8,104,096 B1 | * | 1/2012 | Jenney | 2/67 |
| 2012/0198607 A1 | * | 8/2012 | Lambertz | 2/466 |

* cited by examiner

*Primary Examiner* — Nicholas Lucchesi
*Assistant Examiner* — Kari Petrik
(74) *Attorney, Agent, or Firm* — Richard John Bartz

(57) ABSTRACT

An athletic undergarment has a pants with a trunk and legs. A cup pouch is adjustably attached to a waistband supports a cup protector assembly having a bellows and bladder providing a protective comfortable air cushion for a person's groin area. Adjustable knee supports are attached to the legs.

17 Claims, 7 Drawing Sheets

US 8,398,574 B1

ATHLETIC GARMENT WITH INFLATABLE CUP PROTECTOR ASSEMBLY

CROSS REFERENCE TO RELATED APPLICATION

This application claims the priority benefit of U.S. Provisional Patent Application Ser. No. 61/201,814 filed Dec. 15, 2008.

FIELD OF THE INVENTION

The invention relates to athletic underwear garments for protecting a person's body during sport activities. The garments are underpants that provide body support and protection from impact forces subjected to a person's body.

BACKGROUND OF THE INVENTION

Body protection garments are used by persons active in recreational activities and sports to reduce injury, scrapes and bruises due to impact forces imparted with balls, pucks, players, hockey and lacrosse sticks, and sliding contact with the ground. These garments include pants provided with pads that absorb and distribute impact forces applied thereto. An example of a sports pants with protective pads is disclosed by J T Ross in U.S. Pat. No. 5,134,726. This sport pants has a trunk and legs of elastic stretchable material with pockets in the groin, hip and knee areas. Protective pads of resilient foam material located in the pockets are removable for washing the pants.

SUMMARY OF THE INVENTION

The invention comprises an underwear pants having an adjustable cup pouch for retaining a cup protection assembly to provide a person with comfortable body support and protection. The cup protector assembly has a bladder inflatable with air pressure generated with a manually operated bellows located within the cup pouch. Releasable fasteners secure the cup pouch to the pants to allow the person to alter the vertical and lateral locations of the pouch and bladder for each person for maximum comfort, support and protection. An actuator combined with one-way valve selectively maintains the air pressure in the bladder and allows the air in the bladder to exit the atmosphere. The pants include legs with adjustable knee supports to support and protect a person's knees. The knee supports advantageously retain knee pads in baseball catcher pants.

The cup protector assembly positioned within the cup pouch has an upright concave curved body having a generally semi-circular shaped upper end and side walls that converge to a rounded lower end. A bellows in the shape of a rubber ball that is movable between expanded and compressed positions to pump air under pressure to a bladder having expandable walls and an internal air chamber. A first air inlet one-way valve connected to the bellows only allows air to flow into the bellows when the bellows moves from the contracted position to the expanded position. A second air exit one-way valve connected to the bellows and bladder is operable to allow air to flow out of the bellows and into the bladder and hold the air under pressure in the bladder when the bellows is moved to the compressed position thereby expanding the bladder in the cup pouch. A movable actuator operably associated with the second valve is manually moved to a position that allows air to flow out of the bladder to atmosphere to deflate the bladder.

DESCRIPTION OF PREFERRED EMBODIMENT

Figure 1:
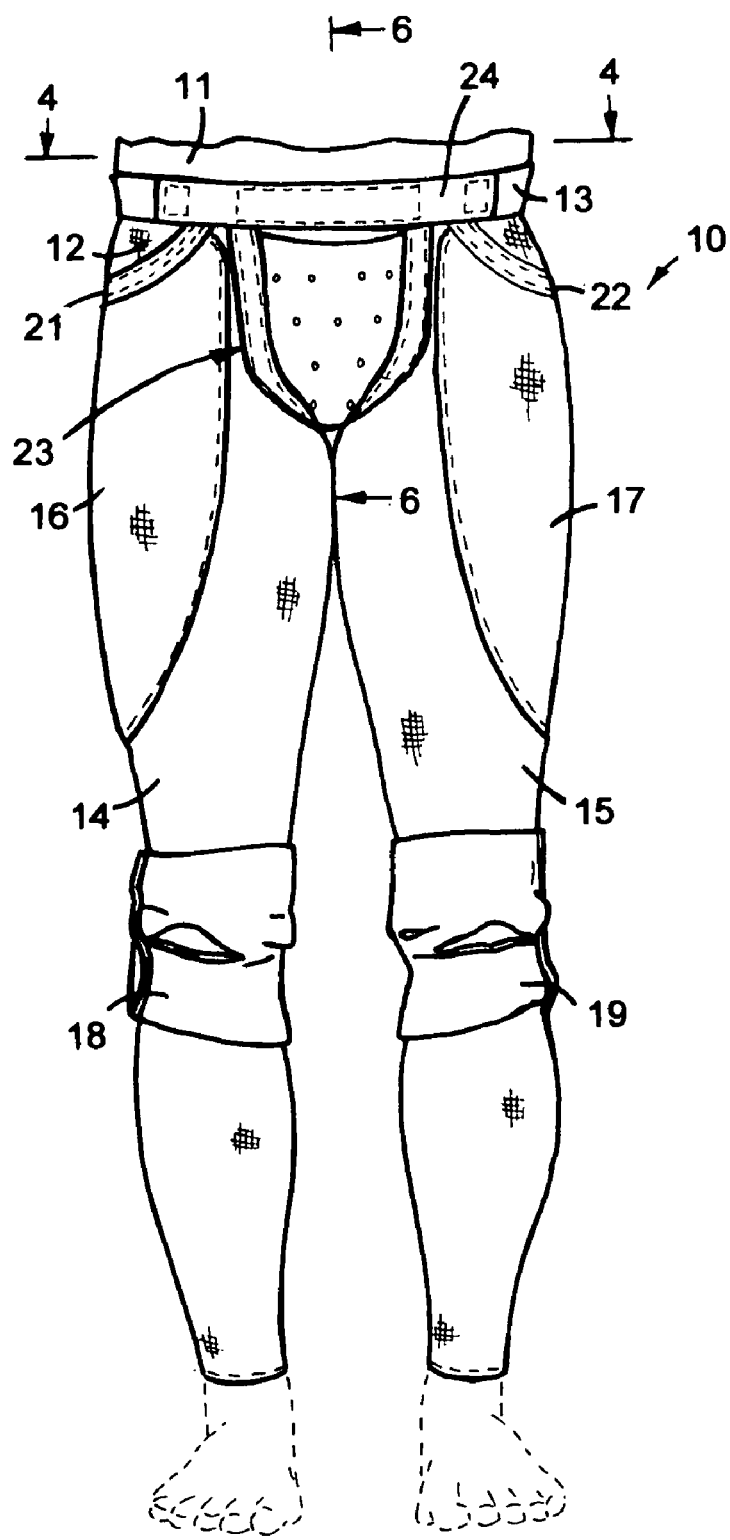
FIG. 1 is a front elevational view of an athletic garment and inflatable cup protector of the invention with the lower portion of a person shown in broken lines.
Figure 2:
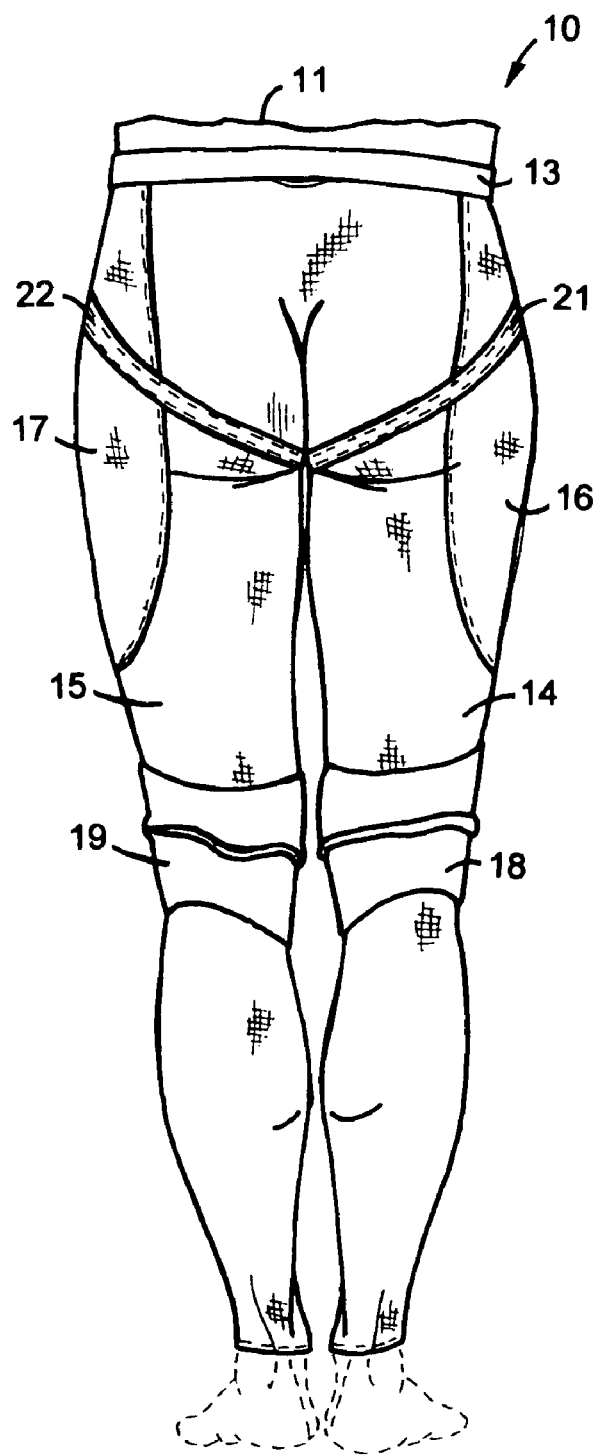
FIG. 2 is a rear elevational view of the garment of FIG. 1.
Figure 3:
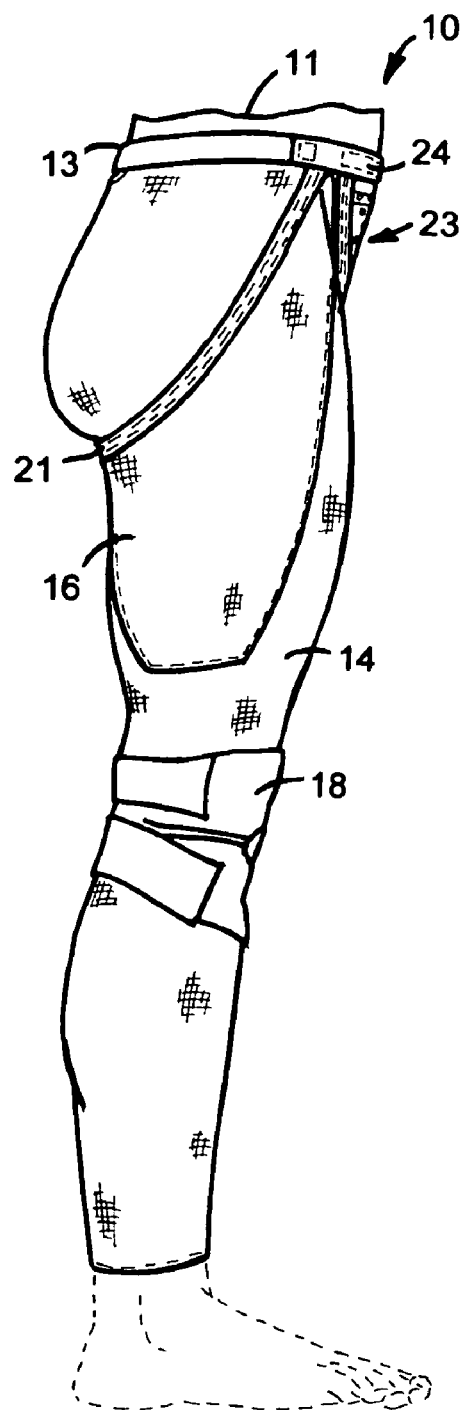
FIG. 3 is side elevational view of the garment of FIG. 1.
Figure 4:
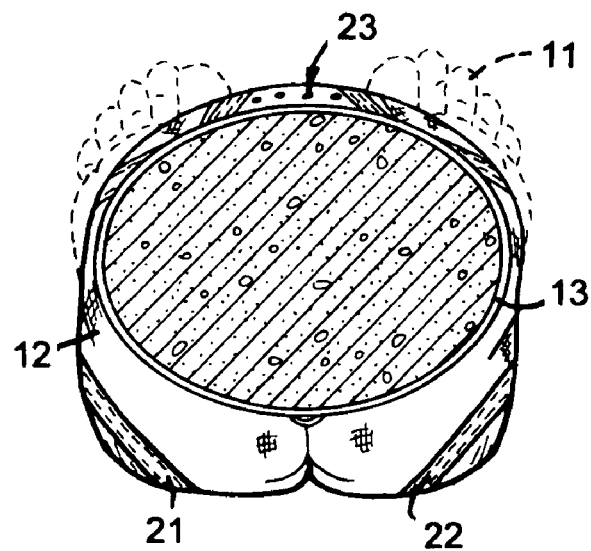
FIG. 4 is a sectional view taken along the line 4-4 of FIG. 1.
Figure 5:
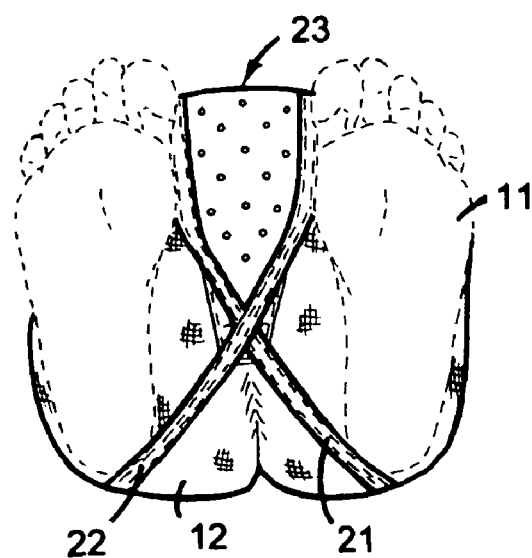
FIG. 5 is a bottom plan view of the garment of FIG. 1.
Figure 6:
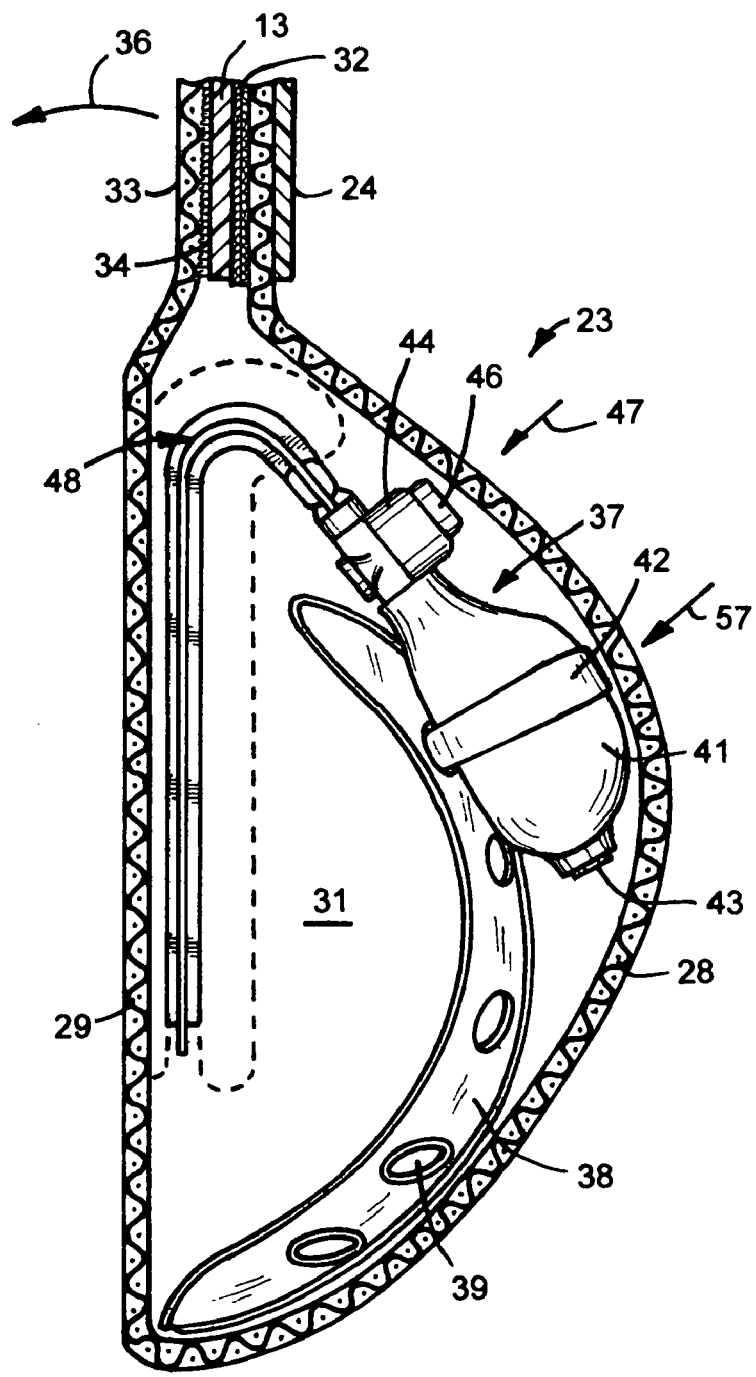
FIG. 6 is an enlarged sectional view taken along the line 6-6 of FIG. 1.
Figure 7:
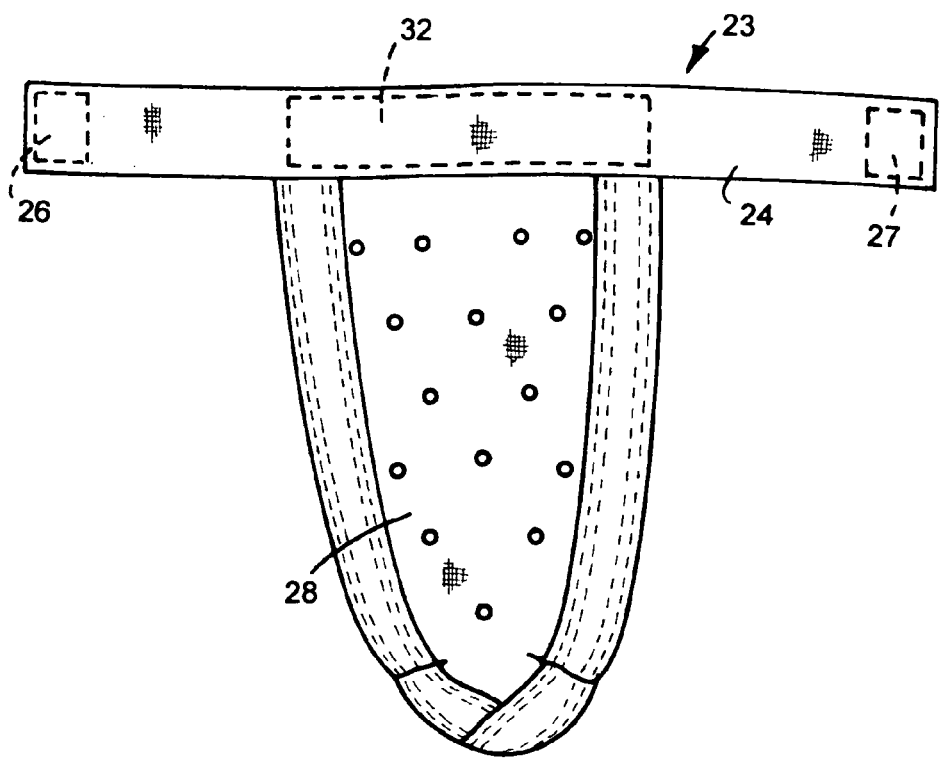
FIG. 7 is an enlarged front elevational view of the cup pouch separated from the garment.
Figure 8:
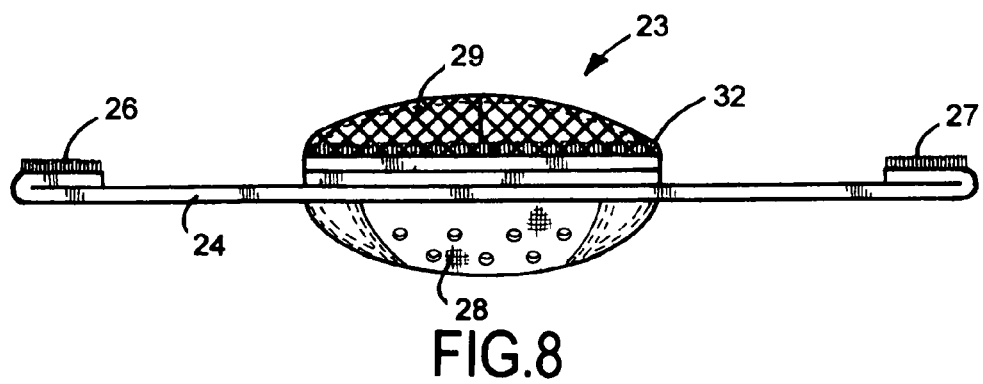
FIG. 8 is a top plan view of FIG. 7.
Figure 9:
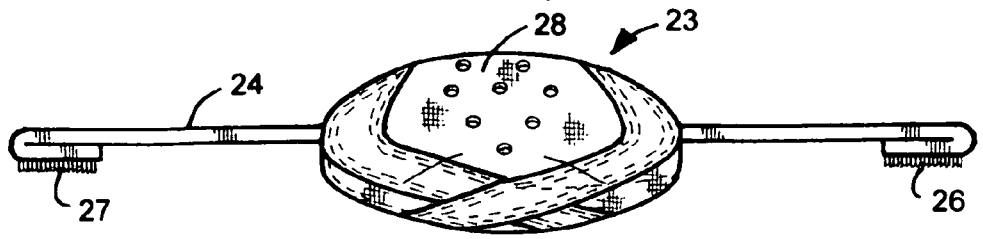
FIG. 9 is a bottom plan view of FIG. 7.

The athletic garment of the invention, shown in FIGS. 1 to 3, is a protective undergarment sport pants for use by baseball, hockey and lacrosse players to provide support and protection of the player's body. Garment 10 has a trunk 12 located around the waist of a person 11. An elastic waistband 13 secured to the top of trunk 12 surrounds the person's waist. Waistband 13 has an elastic compression fit on the person's waist so as to hold garment 10 in a comfortable position on the person. A pair of tubular legs 14 and 15 extend downward from trunk 12 to the person's feet. Legs 14 and 15 in a modification of the garment terminate at a person's knees. Trunk 12 and legs 14 and 15 is a 4-way stretch compression material, such as a polyester neoprene material. Other fabrics can be used for trunk 12 and legs 14 and 15. Hip pads or cushions 16 and 17 are secured to opposite sides of trunk 12 and extend downward on the outside portions of legs 16 and 17. Knee pad supports or holders 18 and 19 operable to retain pads in front of a person's knees are attached to the knee sections of legs 14 and 15. Holders 18 and 19, as shown in FIG. 2, each have a pair of straps extended around the knee sections of legs 14 and 15. Releasable fasteners, such as hook and loop members, retain holders 18 and 19 and knee pads in compression fits around a person's knees. Additional support for holding garment 10 on the person are provided with a pair of elastic straps or webs 21 and 22. Straps 21 and 22, as seen in FIGS. 1, 2, 3 and 5, extend from the front of waistband 13 down and around the back of trunk 12.

An adjustable cup pouch, indicated generally at 23, is connected to the front of waistband 13 with releasable fasteners 26 and 27 secured to an elastic web 24, shown in FIGS. 6 to 9. Band 13 has loop pads that cooperate with fasteners 26 and 27 to adjust the vertical and lateral positions of cup pouch 23 on band 13 to provide a fit that is comfortable and unrestrictive on a person's lower body. Cup pouch 23 has an open mesh fabric front wall 28 joined to a rear wall 29 that encompasses an internal chamber 31. The upper end of front wall 28 is secured to web 24. A releasable fastener 32 attaches web 24 and front wall 28 to band 32. Rear wall 29 has an upper end 33 attached with a releasable fastener 34 to band 13. The upper end 33 of rear wall 29 is manually pulled away from band 13, as shown by arrow 36, to provide an entrance opening into internal chamber 31. End 33 is moved back into holding engagement with fastener 34 to close the opening into chamber 31.

Figure 10:
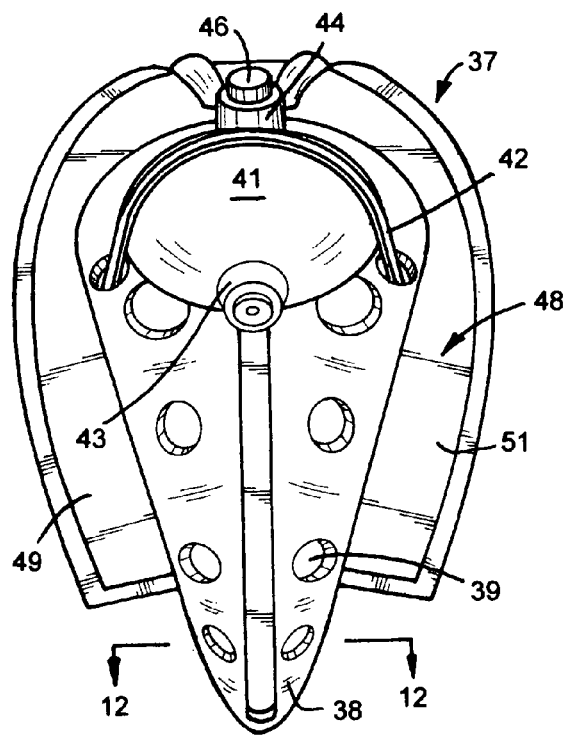
FIG. 10 is a front elevational view of the inflatable cup protector shown in FIG. 6.
Figure 12:
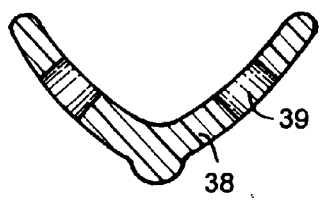
FIG. 12 is an enlarged sectional view taken along the line 12-12 of FIG. 10.
Figure 11:
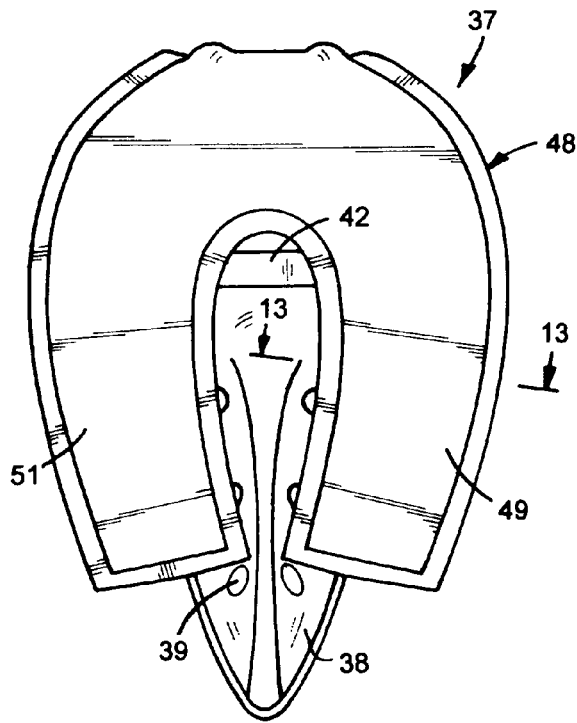
FIG. 11 is a rear elevational view of the inflatable cup protector shown in FIG. 10.
Figure 13:
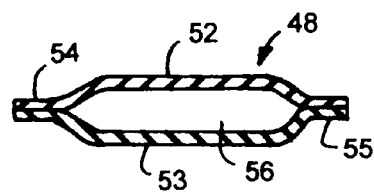
FIG. 13 is an enlarged sectional view taken along the line 13-13 of FIG. 11.

A cup protector assembly 37 located in chamber 31 is retained in an upright functioning position to provide comfortable protection of the groin and crotch area of a person's body. Cup pouch 23 being adjustable on band 13 allows the person to place cup protector assembly 37 in a selected position for effective body protection and comfort. Cup protection assembly 37 has an upright convex curved body 38 having a generally convex curved cross section with a plurality of rows of holes 39. The upper end of body 38 has a semi-circular shape and opposite side edges that converge to a rounded lower end. Body 38 is a flexible plastic member. Other materials, such as rubber and composites, can be used to construct body 38. A bellows 41 is secured with a strap 42 to the outside of the upper end of body 38. Bellows 41 is a hollow rubber ball having an internal air chamber. Bellows 41 can have different shapes and materials. A one-way air inlet valve 43 connected to the lower end of bellows 41 allows air to flow into bellows 41 and prevent back flow of air out of bellows 41. The upper end of bellows 41 is connected to a one-way air exhaust valve 44 having an air pressure release actuator 46. When bellows 41 is compressed by an external manual force, shown by arrows 57 in FIG. 6, air is forced out of bellows 41 through valve 44 and into bladder 48. In use actuator 46 is pressed with an external force, shown by arrow 47, to an air release position allowing air to flow out of bladder 48 to atmosphere. Actuator 46 is a movable valving member that is normally in a one-way air flow operating position allowing air to flow from bellows 41 into a bladder 48 located behind body 38 in chamber 31 of pouch 23. Bladder 48 is an expandable flexible member that increases in size in chamber 31, shown in broken lines in FIG. 6, in response to an increase in air pressure in the interior chamber of the bladder. The inflated bladder 48 is an air cushion for impact forces subjected to adjustable cup pouch 23 and cup protector assembly 37. As shown in FIGS. 10, 11 and 13, bladder 48 has an inverted U-shape with downwardly and inwardly directed tubular members 49 and 51 located adjacent the side edges of body 38. The upper center portion of bladder 48 is attached to air exhaust valve 44 that allows air to flow from bellows 41 into bladder 48 and to allow air to flow out of bladder 48 to atmosphere. As shown in FIG. 13, bladder 48 has flexible and expandable inner and outer walls 52 and 53 with adjacent inner and outer peripheral edges 54 and 55 sealed or joined together to enclose an internal chamber 56. Walls 52 and 53 are air impervious expandable rubber sheets having heat or sonic sealed adjacent peripheral edges. Walls 52 and 53 can be made of other materials including, but not limited to, plastics.

There has been described and illustrated in the drawings embodiment of the athletic garment with an adjustable cup pouch and cup protector assembly. Changes in materials, structures and arrangement of structures can be made by persons skilled in the art without departing from the invention.

The invention claimed is:

1. An athletic garment comprising:
   a pants having a trunk and legs;
   a cup pouch having an internal chamber;
   at least one fastener attaching the cup pouch to the trunk; and
   a cup protector assembly located within the internal chamber of the cup pouch;
   said cup protector assembly including
   a bellows movable between expanded and compressed positions to allow air to flow into the bellows and to pump air out of the bellows, and
   a bladder connected to the bellows for receiving air from the bellows to inflate the bladder.

2. The garment of claim 1 wherein:
   the pants includes a waistband connected to the trunk, and
   said fastener comprising a releasable fastener attachable to the waistband in selected positions to adjust the position of the cup pouch on the trunk of the pants.

3. The garment of claim 1 including:
   knee portions included on said legs; and
   knee pad holders attached to the knee portions of the legs of the pants.

4. The garment of claim 1 including:
   a first one-way valve connected to the bellows operable to only allow air to flow into the bellows when the bellows moves from the compressed position to the expanded position; and
   a second one-way valve connected to the bellows and bladder operable to allow air to flow out of the bellows and into the bladder to inflate the bladder and hold the air in the bladder when the bellows is moved from the expanded position to the compressed position thereby inflating the bladder with air.

5. The garment of claim 4 including:
   an actuator operatively associated with the second one-way valve to allow air to flow out of the bladder to atmosphere.

6. The garment of claim 1 including:
   a body located in the internal chamber adjacent the bladder.

7. The garment of claim 6 wherein:
   the body is a concave curved member having a generally semi-circular shaped upper end and downwardly converging side edges.

8. The garment of claim 6 wherein:
   the bellows comprises a compressible hollow rubber ball.

9. The garment of claim 6 wherein:
   the bladder includes downwardly extended tubular members having air chambers for accommodating air under pressure from the bellows whereby the tubular members expand adjacent the body.

10. The garment of claim 9 wherein:
    each tubular member has flexible and expandable walls around an air chamber.

11. The garment of claim 1 including:
    knee portions included on said legs,
    knee pads holders attached to the knee portions of the legs of the pants, said holders having
    knee pads,
    supports for holding the pads, and
    releasable fasteners for retaining the supports and pads in a compression fit around a person's knees.

12. An athletic garment comprising:
    a pants having a trunk with a waistband and legs;
    a cup pouch having an internal chamber;
    releasable fasteners connecting the cup pouch to the waistband to allow vertical and lateral adjustment of the positions of the cup pouch on the waistband;
    a cup protector assembly located within the internal chamber of the cup pouch, said cup protector assembly including:
    an upright body,
    a bellows movable between expanded and compressed positions to allow air to flow into the bellows and to pump air out of the bellows, a bladder located adjacent the body, said bladder being connected to the bellows for receiving air from the bellows to inflate the bladder, a first one-way valve connected to the bellows operable to only allow air to flow into the bellows when the bellows moves from the compressed position to the expanded position;

a second one-way valve connected to the bellows and bladder operable to allow air to flow out of the bellows and into the bladder to inflate the bladder and hold air in the bladder when bellows is moved from the expanded position to the compressed position thereby inflating the bladder with air; and an actuator included with the second one-way valve operable to allow air to flow out of the bladder to atmosphere.

13. The garment of claim 12 wherein:
the body is a concave curved member having a generally semi-circular shaped upper end and downwardly converging side edges.

14. The garment of claim 12 wherein:
the bellows comprises a compressible hollow rubber ball.

15. The garment of claim 12 wherein:
the bladder includes downwardly extended tubular members having air chambers for accommodating air under pressure from the bellows whereby the tubular members expand adjacent the body.

16. The garment of claim 15 wherein:
each tubular member has flexible and expandable walls around an air chamber.

17. The garment of claim 12 including:
knee portions included on said legs,
knee pads holders attached to the knee portions of the legs of the pants, said holders having
knee pads,
supports for holding the pads, and
releasable fasteners for retaining the supports and pads in a compression fit around a person's knees.

* * * * *